United States Patent [19]

Billington et al.

[11] Patent Number: 5,294,618

[45] Date of Patent: Mar. 15, 1994

[54] OCTAHYDROBENZISOQUINOLINE DERIVATIVES AS ANTIPSYCHOTIC AGENTS

[75] Inventors: David C. Billington, Bishops Stortford; Michael G. N. Russell, Welwyn Garden City, both of England

[73] Assignee: Merck Sharp & Dohme Limited, Hoddesdon, United Kingdom

[21] Appl. No.: 17,367

[22] Filed: Feb. 11, 1993

Related U.S. Application Data

[63] Continuation of Ser. No. 914,653, Jul. 15, 1992, abandoned, which is a continuation of Ser. No. 774,659, Oct. 15, 1991, abandoned, which is a continuation of Ser. No. 555,708, Jul. 23, 1990, abandoned.

[30] Foreign Application Priority Data

Jul. 28, 1989 [GB] United Kingdom ............... 8917333

[51] Int. Cl.$^5$ ............... C07D 217/04; A61K 31/47
[52] U.S. Cl. ............... 514/290; 514/287; 546/65; 546/101
[58] Field of Search ............... 546/65, 101; 514/287, 514/290

[56] References Cited

U.S. PATENT DOCUMENTS

| | | | |
|---|---|---|---|
| 4,740,602 | 4/1988 | Bottcher et al. | 548/406 |
| 5,049,564 | 9/1991 | De Bernardis | 514/290 |

FOREIGN PATENT DOCUMENTS

| | | |
|---|---|---|
| 0106486 | of 0000 | European Pat. Off. |
| 0127597 | of 0000 | European Pat. Off. |
| 1596170 | 8/1981 | United Kingdom |
| 2126584 | 3/1984 | United Kingdom |

OTHER PUBLICATIONS

Cannon et al, *J. Med. Chem.*, vol. 19, No. 8, (1976), pp. 987-993.

Cannon et al, *J. Med. Chem.*, vol. 22, No. 4 (1979), pp. 341-347.

Cannon et al, *J. Med. Chem.*, vol. 23, No. 1 (1980) pp. 1-5.

Hahne et al., Arch. Pharm. (Weinheim) (1979), 312, 472-477.

Kumar et al, Indian J. Chem., Sec. B (1979), 17, 239-243.

Menard et al, Canadian Journal of Chemistry 52, No. 12 (1974), pp. 2316-2326.

*Primary Examiner*—Mukund J. Shah
*Assistant Examiner*—Philip I. Datlow
*Attorney, Agent, or Firm*—Robert J. North; Joseph F. DiPrima

[57] ABSTRACT

A class of 1,2,3,4,4a,5,6,10b-octahydrobenz[f]isoquinoline compounds and pharmaceutically acceptable salts of formula I:

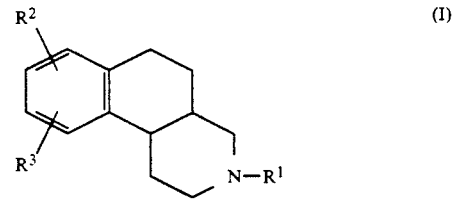

wherein, $R^1$ represents hydrocarbon;

$R^2$ and $R^3$ independently represent hydrogen, hydrocarbon, halogen, cyano, trifluoromethyl, nitro, $-OR^x$, $-SR^x$, $-NR^xR^y$, $-CO_2R^x$ or together represent methylenedioxy; and $R^x$ and $R^y$ independently represent hydrogen or hydrocarbon.

The compounds disclosed herein are selective ligands at sigma recognition sites and are therefore useful in the treatment of psychiatric disorders.

13 Claims, No Drawings

OCTAHYDROBENZISOQUINOLINE DERIVATIVES AS ANTIPSYCHOTIC AGENTS

This is a continuation of application Ser. No. 07/914,653, filed on Jul. 15, 1992, now abandoned, which is a continuation of application Ser. No. 07/774,659, filed Oct. 15, 1991, now abandoned, which is a continuation of application Ser. No. 555,708, filed Jul. 23, 1990, now abandoned.

This invention relates to a class of octahydrobenz[f]isoquinoline derivatives which are selective ligands at sigma recognition sites and are therefore useful as neuroleptic agents.

Certain octahydrobenz[f]isoquinoline derivatives are known. For example, the preparation of 3-methyl-1,2,3,4,4a,5,6,10b-octahydrobenz[f]isoquinoline, by hydrogenation of the corresponding 4a,10b-unsaturated derivative, is described in *Arch. Pharm.* (*Weinheim*), 1979, 312, 472. No therapeutic utility for 3-methyl-1,2,3,4,4a,5,6,10b-octahydrobenz[f]isoquinoline is disclosed, although the 3,10b-dimethyl homologue, also described therein, is stated to produce central analgesic effects. The preparation of 3-[3-(4-fluorobenzoyl)-propyl]-1,2,3,4,4a,5,6,10b-octahydrobenz[f]isoquinoline is described in *Indian J. Chem., Sect. B,* 1979, 17, 239. This compound, which is prepared by alkylating the corresponding N-unsubstituted derivative, is stated to have weak CNS depressant activity and significant hypotensive activity. Neither of the aforementioned documents discloses or suggests neuroleptic activity for the octahydrobenz[f]isoquinoline derivatives described therein.

GB-1596170 describes a class of 1,2,3,4,4a,10b-hexahydrobenz[f]isoquinolines which are stated to have neuroleptic effects. However, these compounds also display sedative side-effects, rendering them unsuitable for use solely as neuroleptics.

U.S. Pat. No. 4,740,602 describes a class of compounds containing an indol-3-yl ring system and inter alia a 1,2,3,4,5,6-hexahydrobenz[f]isoquinolin-3-yl ring system, the two ring systems being separated by a $C_{2-5}$ alkylene chain or a bridging chain of formula —CH$_2$—S(O)$_x$—CH$_2$CH$_2$—, in which x is zero, 1 or 2. These compounds are stated to exhibit inter alia neuroleptic properties. However, analgesic and hypotensive side-effects are also mentioned for these compounds, detracting from any specificity they might possess as neuroleptics.

Most of the numerous currently available clinically effective antipsychotic drugs are dopamine $D_2$ receptor antagonists. As a result, they produce a characteristic spectrum of undesirable side-effects. These include endocrine effects and extrapyramidal side-effects, as well as often irreversible tardive dyskinesia. In addition, $D_2$ receptor antagonists are only palliative. They tend to alleviate only certain schizophrenic behaviour, especially the "positive" symptoms of florid delusions and hallucinations, with much less effect on the "negative" symptoms of emotional withdrawal.

From receptor binding studies, it has been shown that many effective neuroleptic agents are ligands at sigma recognition sites in the brain. Various compounds are known which are capable of interacting with the sigma recognition site, and it is considered that this interaction is significant in the manifestation of their neuroleptic properties. Most of these compounds, however, also display significant activity at the dopamine $D_2$ receptor and consequently elicit the undesirable side-effects referred to above. For example, haloperidol, a widely used neuroleptic agent, interacts equally potently with sigma sites and $D_2$ receptors.

One compound which is essentially inactive at dopamine $D_2$ receptors is rimcazole. However, whilst showing some antischizophrenic activity, rimcazole displays only moderate potency at sigma sites.

The analgesic compound N-allylnormetazocine (SKF 10047), whilst having an affinity for the sigma recognition site, also interacts strongly with the N-methyl-D-aspartate (NMDA) ion-channel complex, and thereby evokes a variety of psychotic symptoms including disorientation, excitement and hallucinations.

We have now found a class of potent, selective sigma receptor antagonists displaying negligible activity at $D_2$, NMDA and other CNS receptors, which are therefore of value as neuroleptic agents.

The present invention accordingly provides the use of a compound of formula I or a pharmaceutically acceptable salt thereof:

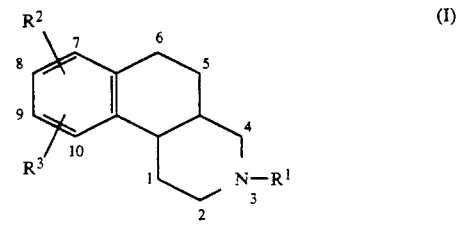

(I)

wherein
$R^1$ represents hydrocarbon;
$R^2$ and $R^3$ independently represent hydrogen, hydrocarbon, halogen, cyano, trifluoromethyl, nitro, —OR$^x$, —SR$^x$, —NR$^x$R$^y$, —CO$_2$R$^x$ or —CONR$^x$R$^y$, or together represent methylenedioxy; and
$R^x$ and $R^y$ independently represent hydrogen or hydrocarbon;

for the manufacture of a medicament for the treatment and/or prevention of psychiatric disorders.

The term "hydrocarbon" as used herein includes straight-chained, branched and cyclic groups, including heterocyclic groups, containing up to 18 carbon atoms, suitably up to 15 carbon atoms, and conveniently up to 12 carbon atoms. Suitable hydrocarbon groups include $C_{1-6}$ alkyl, $C_{2-6}$ alkenyl, $C_{2-6}$ alkynyl, $C_{3-10}$ cycloalkyl, $C_{3-7}$ cycloalkyl($C_{1-6}$)alkyl, aryl, aryl($C_{1-6}$)alkyl, $C_{3-7}$ heterocycloalkyl, $C_{3-7}$ heterocycloalkyl($C_{1-6}$)alkyl, heteroaryl and heteroaryl($C_{1-6}$)alkyl.

Suitable alkyl groups include straight-chained and branched alkyl groups containing from 1 to 6 carbon atoms. Typical examples include methyl and ethyl groups, and straight-chained or branched propyl and butyl groups. Particular alkyl groups are n-propyl, iso-propyl, n-butyl and t-butyl.

Suitable alkenyl groups include straight-chained and branched alkenyl groups containing from 2 to 6 carbon atoms. Typical examples include vinyl, allyl, dimethylallyl and butenyl groups.

Suitable alkynyl groups include straight-chained and branched alkynyl groups containing from 2 to 6 carbon atoms. Typical examples include ethynyl and propargyl groups.

Suitable cycloalkyl groups include groups containing from 3 to 10 carbon atoms. Particular cycloalkyl groups are cyclopropyl, cyclohexyl and adamantyl.

Suitable aryl groups include phenyl and naphthyl groups.

Particular aryl($C_{1-6}$)alkyl groups are benzyl, phenethyl, phenylpropyl and naphthylmethyl.

Suitable heterocycloalkyl groups include pyrrolidinyl, piperidyl, piperazinyl and morpholinyl groups.

Suitable heteroaryl groups include pyridyl, quinolyl, isoquinolyl, pyridazinyl, pyrimidinyl, pyrazinyl, pyranyl, furyl, benzofuryl, thienyl, benzthienyl, imidazolyl, oxadiazolyl and thiadiazolyl groups. Particular heteroaryl groups are pyridyl, furyl and thienyl.

The hydrocarbon group may in turn be optionally substituted by one or more groups selected from $C_{1-6}$ alkyl, adamantyl, phenyl, halogen, $C_{1-6}$ haloalkyl, trifluoromethyl, hydroxy, $C_{1-6}$ alkoxy, aryloxy, keto, $C_{1-3}$ alkylenedioxy, nitro, cyano, carboxy, $C_{2-6}$ alkoxycarbonyl, $C_{2-6}$ alkoxycarbonyl($C_{1-6}$)alkyl, $C_{2-6}$ alkylcarbonyloxy, optionally substituted arylcarbonyloxy, $C_{2-6}$ alkylcarbonyl, optionally substituted arylcarbonyl, $C_{1-6}$ alkylthio, $C_{1-6}$ alkylsulphinyl, $C_{1-6}$ alkylsulphonyl, amino, mono- or di($C_{1-6}$)alkylamino, $C_{2-6}$ alkylcarbonylamino and $C_{2-6}$ alkoxycarbonylamino.

The term "halogen" as used herein includes fluorine, chlorine, bromine and iodine, especially chlorine.

In a further aspect, the invention provides a pharmaceutical composition comprising a compound of formula IA or a pharmaceutically acceptable salt thereof:

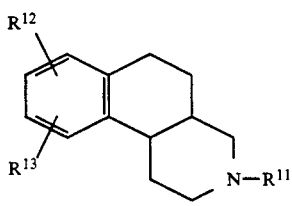

(IA)

wherein $R^{11}$ represents hydrocarbon;

$R^{12}$ and $R^{13}$ independently represent hydrogen, hydrocarbon, halogen, cyano, trifluoromethyl, nitro, $-OR^x$, $-SR^x$, $-NR^xR^y$, $-CO_2R^x$ or $-CONR^xR^y$, or together represent methylenedioxy; and $R^x$ and $R^y$ independently represent hydrogen or hydrocarbon;

provided that $R^{12}$ and $R^{13}$ do not simultaneously represent hydrogen when $R^{11}$ represents 3-(4-fluorobenzoyl)propyl;

in association with one or more pharmaceutically acceptable carriers and/or excipients.

The invention also provides a compound of formula IA as defined above or a pharmaceutically acceptable salt thereof for use in therapy.

Certain compounds falling within the definition of formula I above are novel. Accordingly, in a still further aspect the present invention provides a compound of formula II or a salt thereof:

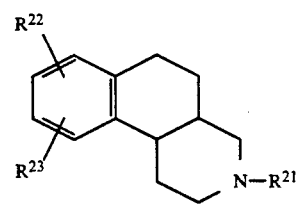

(II)

wherein $R^{21}$ represents hydrocarbon;

$R^{22}$ and $R^{23}$ independently represent hydrogen, hydrocarbon, halogen, cyano, trifluoromethyl, nitro, $-OR^x$, $-SR^x$, $-NR^xR^y$, $-CO_2R^x$ or $-CONR^xR^y$, or together represent methylenedioxy; and $R^x$ and $R^y$ independently represent hydrogen or hydrocarbon;

provided that $R^{22}$ and $R^{23}$ do not simultaneously represent hydrogen when $R^{21}$ represents methyl or 3-(4-fluorobenzoyl)propyl.

For use in medicine, the salts of the compounds of formula II will be non-toxic pharmaceutically acceptable salts. Other salts may, however, be useful in the preparation of the compounds according to the invention or of their non-toxic pharmaceutically acceptable salts.

Suitable pharmaceutically acceptable salts of the compounds of formulae I, IA and II above include acid addition salts which may, for example, be formed by mixing a solution of the compound according to the invention with a solution of a pharmaceutically acceptable non-toxic acid such as hydrochloric acid, fumaric acid, maleic acid, succinic acid, acetic acid, citric acid, tartaric acid, carbonic acid or phosphoric acid.

Suitable values for the substituent $R^{21}$ in the compounds of formula II above include optionally substituted $C_{3-6}$ alkyl, for example n-propyl or n-butyl; optionally substituted $C_{2-6}$ alkenyl, for example allyl, dimethylallyl or butenyl; optionally substituted $C_{3-10}$ cycloalkyl, for example cyclohexyl or adamantyl; optionally substituted $C_{3-7}$ cycloalkyl ($C_{1-6}$)alkyl, for example cyclopropylmethyl or cyclohexylmethyl; optionally substituted aryl($C_{1-6}$)alkyl, for example benzyl, methylbenzyl, t-butylbenzyl, chlorobenzyl, nitrobenzyl, methoxybenzyl, phenethyl, (nitrophenyl)ethyl, phenylpropyl or naphthylmethyl; and optionally substituted heteroaryl ($C_{1-6}$)alkyl, for example furylmethyl, thienylmethyl or picolyl.

Examples of the substituents $R^{22}$ and $R^{23}$ in the compounds of formula II above include hydrogen, halogen, $C_{1-6}$ alkyl and $C_{1-6}$ alkoxy. Suitably one of $R^{22}$ and $R^{23}$ represents hydrogen and the other represents hydrogen, chlorine, methyl or methoxy, especially hydrogen, methyl or methoxy; or $R^{22}$ and $R^{23}$ both represent methyl or methoxy, especially methyl. Preferably, $R^{22}$ and $R^{23}$ both represent hydrogen.

When $R^{22}$ and $R^{23}$ in the compounds of formula II above are other than hydrogen, they may be present at any desired position of the aromatic moiety. In a particular embodiment, these non-hydrogen groups $R^{22}$ and $R^{23}$ are present at positions 7 and 9 of the octahydrobenz[f]isoquinoline structure.

The compounds of formulae I, IA and II above have at least two asymmetric centres, and may accordingly exist both as enantiomers and as diastereoisomers. In particular, the ring junction at positions 4a and 10b of the octahydrobenz[f]isoquinoline ring system may be cis or trans. It is to be understood that all such isomers and mixtures thereof are encompassed within the scope of the present invention.

Preferred compounds of formula II above are those wherein the ring junction at positions 4a and 10b is trans.

One sub-class of compounds according to the invention is represented by the compounds of formula IIA and salts thereof:

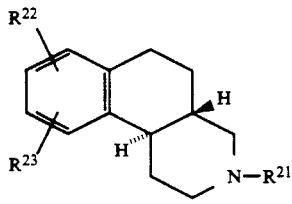

(IIA)

wherein $R^{21}$, $R^{22}$ and $R^{23}$ are as defined above with reference to formula II; in particular wherein $R^{21}$ represents $C_{3-6}$ alkyl, $C_{2-6}$ alkenyl, $C_{3-7}$ cycloalkyl, $C_{3-7}$ cycloalkyl($C_{1-6}$)alkyl, aryl($C_{1-6}$)alkyl or heteroaryl($C_{1-6}$)alkyl, any of which groups may be optionally substituted. Preferred values of $R^{21}$ in the compounds of formula IIA are n-propyl, n-butyl, allyl, dimethylallyl, butenyl, cyclohexyl, adamantyl, cyclopropylmethyl, benzyl, methylbenzyl, t-butylbenzyl, chlorobenzyl, nitrobenzyl, methoxybenzyl, phenethyl, (nitrophenyl)ethyl, phenylpropyl, naphthylmethyl, furylmethyl, thienylmethyl and picolyl.

A further sub-class of compounds according to the invention is represented by the compounds of formula IIB and salts thereof:

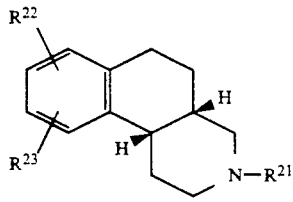

(IIB)

wherein $R^{21}$, $R^{22}$ and $R^{23}$ are as defined above with reference to formula II; in particular wherein $R^{21}$ represents $C_{3-6}$ alkyl, especially n-butyl.

Specific compounds within the scope of the present invention include:
3-butyl-1,2,3,4,4a,5,6,10b-octahydrobenz[f]isoquinoline;
3-(4'-methoxybenzyl)-1,2,3,4,4a,5,6,10b-octahydrobenz[f]isoquinoline;
3-cyclohexyl-1,2,3,4,4a,5,6,10b-octahydrobenz[f]isoquinoline;
3-benzyl-1,2,3,4,4a,5,6,10b-octahydrobenz[f]isoquinoline;
1,2,3,4,4a,5,6,10b-octahydro-3-phenethylbenz[f]isoquinoline;
1,2,3,4,4a,5,6,10b-octahydro-3-(2'-picolyl)benz[f]isoquinoline;
3-(4'-nitrobenzyl)-1,2,3,4,4a,5,6,10b-octahydrobenz[f]isoquinoline;
3-(4'-chlorobenzyl)-1,2,3,4,4a,5,6,10b-octahydrobenz[f]isoquinoline;
3-(4'-t-butylbenzyl)-1,2,3,4,4a,5,6,10b-octahydrobenz[f]isoquinoline;
3-[2'-(4-nitrophenyl)ethyl]-1,2,3,4,4a,5,6,10b-octahydrobenz[f]isoquinoline;
1,2,3,4,4a,5,6,10b-octahydro-3-(3'-phenylpropyl)benz[f]isoquinoline;
3-(3'-methylbut-2'-enyl)-1,2,3,4,4a,5,6,10b-octahydrobenz[f]isoquinoline;
1,2,3,4,4a,5,6,10b-octahydro-3-(prop-2'-enyl)benz[f]isoquinoline;
3-(but-3'-enyl)-1,2,3,4,4a,5,6,10b-octahydrobenz[f]isoquinoline;
1,2,3,4,4a,5,6,10b-octahydro-3-(2'-thienylmethyl)benz[f]isoquinoline;
3-(2'-furylmethyl)-1,2,3,4,4a,5,6,10b-octahydrobenz[f]isoquinoline;
1,2,3,4,4a,5,6,10b-octahydro-3-propylbenz[f]isoquinoline; 3-(1'-adamantyl)-1,2,3,4,4a,5,6,10b-octahydrobenz[f]isoquinoline;
3-(2'-adamantyl)-1,2,3,4,4a,5,6,10b-octahydrobenz[f]isoquinoline;
3-butyl-7,9-dimethyl-1,2,3,4,4a,5,6,10b-octahydrobenz[f]isoquinoline;
3-(2'-naphthylmethyl)-1,2,3,4,4a,5,6,10b-octahydrobenz[f]isoquinoline;
3-cyclopropylmethyl-1,2,3,4,4a,5,6,10b-octahydrobenz[f]isoquinoline;
and salts thereof.

The pharmaceutical compositions of this invention are preferably in unit dosage forms such as tablets, pills, capsules, powders, granules, sterile parenteral solutions or suspensions, or suppositories, for oral, parenteral or rectal administration. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

In the treatment of psychiatric disorders, a suitable dosage level is about 0.01 to 250 mg/kg per day, preferably about 0.05 to 100 mg/kg per day, and especially about 0.05 to 5 mg/kg per day. The compounds may be administered on a regimen of 1 to 4 times per day.

The compounds of formula I above, including the novel compounds according to the invention, may be prepared by a process which comprises reacting a compound of formula $R^1$-L with a compound of formula III:

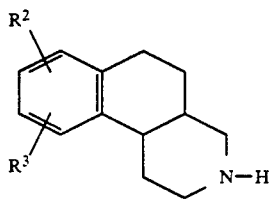

wherein $R^1$, $R^2$ and $R^3$ are as defined above; and L represents a leaving group.

The leaving group L is suitably halogen, for example bromine.

The reaction is conveniently carried out in the presence of a mild base such as potassium carbonate, in a suitable solvent, e.g. N,N-dimethylformamide, suitably at an elevated temperature, for example a temperature in the region of 100° C.

In an alternative process, the compounds of formula I above, including the novel compounds according to the invention, in which $R^1$ is equivalent to a group of formula —$CH_2R^i$, may be prepared by reducing a compound of formula IV:

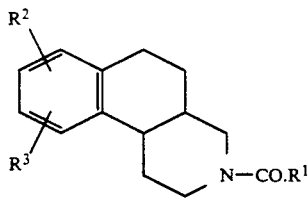

wherein $R^2$ and $R^3$ are as defined above.

A suitable reagent for effecting the reduction of the compounds of formula IV is lithium aluminium hydride.

The intermediates of formula IV may suitably be prepared by reacting a compound of formula III as defined above with an acid halide of formula $R^i$.CO.-Hal, in which Hal represents halogen such as chlorine or bromine.

The intermediates of formula III above may be prepared by a process which comprises reducing a compound of formula V:

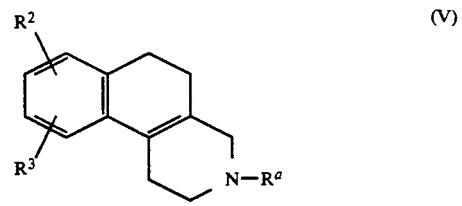

wherein $R^2$ and $R^3$ are as defined above, and $R^a$ represents an amino-protecting group; and subsequently removing the amino-protecting group $R^a$.

Suitable examples of amino-protecting groups for the substituent $R^a$ include carboxylic acid groups such as acetyl, chloroacetyl, trifluoroacetyl, formyl, benzoyl, phthaloyl, phenylacetyl or pyridinecarbonyl; acid groups derived from carbonic acid such as ethoxycarbonyl, benzyloxycarbonyl, t-butoxycarbonyl, biphenylisopropoxycarbonyl, p-methylbenzyloxycarbonyl, p-nitrobenzyloxycarbonyl, p-bromobenzyloxycarbonyl, p-phenylazobenzyloxycarbonyl, p-(p'-methoxyphenylazo)benzyloxycarbonyl or t-amyloxycarbonyl; acid groups derived from sulphonic acid, e.g. p-toluenesulphonic acid; and other groups such as methyl, benzyl, trityl, o-nitrophenylsulphenyl or benzylidene.

Preferred amino-protecting groups are methyl, benzyl, benzyloxycarbonyl and t-butoxycarbonyl.

The removal of the amino-protecting group present in the resultant compound may be effected by an appropriate procedure depending upon the nature of the protecting group. For example, if $R^a$ represents methyl this group may be removed by treatment with cyanogen bromide at an elevated temperature, followed by work-up in a mineral acid such as aqueous hydrochloric acid, also at an elevated temperature.

In a further process, the compounds of formula I above, including the novel compounds according to the invention, may, where appropriate, be prepared directly by reduction of a compound of formula VI:

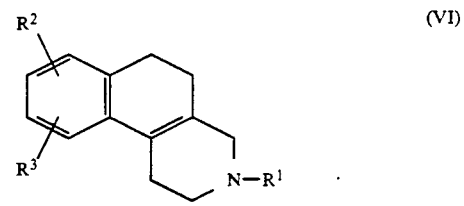

wherein $R^1$, $R^2$ and $R^3$ are as defined above.

The nature of the conditions employed for effecting the reduction of the compounds of formulae V and/or VI will depend on the stereochemistry of the ring junction at positions 4a and 10b desired in the final octahydrobenz[f]isoquinoline product. For example, if the 4a,10b-cis isomer is desired, an appropriate method for reducing the precursor of formula V or VI will be catalytic hydrogenation. A suitable catalyst is platinum(IV) oxide, and the reaction is conveniently carried out in ethanol as solvent.

Alternatively, if the 4a,10b-trans isomer is desired, a suitable reducing agent is lithium in liquid ammonia. The reaction is conveniently carried out in an inert organic solvent such as tetrahydrofuran, preferably in the presence of aniline, and suitably at a temperature in the region of −78° C.

The intermediates of formulae V and VI above may, as appropriate, be prepared analogously to the method described in Can. J. Chem., 1974, 52, 2316. The synthetic route may be illustrated as follows:

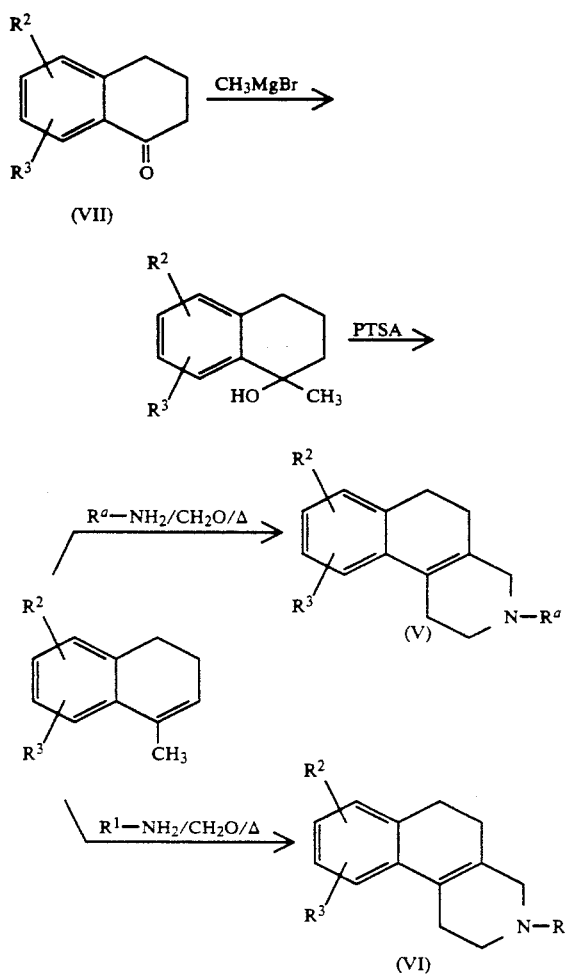

in which $R^1$, $R^2$, $R^3$ and $R^a$ are as defined above; and PTSA is an abbreviation for p-toluenesulphonic acid.

The α-tetralone derivatives of formula VII above, where they are not commercially available, can be prepared by the methods described in J. Org. Chem., 1962, 27, 70, or J. Org. Chem., 1971, 36, 2480, or by methods analogous thereto.

Except where explicitly stated otherwise, the above-described processes are likely to give rise to mixtures of stereoisomers. At an appropriate stage, these isomers may be separated by conventional techniques such as preparative chromatography.

The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-d-tartaric acid and/or (+)-di-p-toluoyl-l-tartaric acid followed by fractional crystallization and regeneration of the free base. The compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in Protective Groups in Organic Chemistry, ed. J. F. W. McOmie, Plenum Press, 1973; and T. W. Greene, Protective Groups in Organic Synthesis, John Wiley & Sons, 1981. The protecting groups may be removed at a convenient subsequent stage using methods known from the art.

Displacement of Tritiated Sigma Ligand

In vitro activity

Binding of test compounds to the sigma site in vitro was determined by the method of Weber et al., Proc. Natl. Acad. Sci. USA, 1986, 83, 8784. The compounds of the accompanying Examples displaced tritiated di-tolyl guanidine (DTG) from sigma sites with potencies better than 200 nM.

In vivo activity

The ability of the test compounds to displace tritiated sigma ligands in vivo was determined by a modification of the method of Ferris et al., Life Sci., 1986, 38, 2329. In these experiments the sigma ligand used was tritiated (+)-SKF 10047. The compounds of accompanying Examples 2 and 4 were tested and showed an effective dose for displacing 50% of ligand ($ED_{50}$), following s.c. dosing, of better than 1.0 mg/kg in each case.

EXAMPLE 1 cis-3-Butyl-1,2,3,4,4a,5,6,10b-octahydrobenz[f]isoquinoline

Step 1:
1-Hydroxy-1-methyl-1,2,3,4-tetrahydronaphthalene

A solution of 98.0 g (0.670 mol) of α-tetralone in 800 ml of anhydrous ether was added over 30 min to a solution of 285 ml (0.855 mol) of 3.0M methyl magnesium bromide in ether under $N_2$ whilst stirring magnetically. After completion of the addition, the reaction was heated to reflux for 30 min, allowed to cool, then quenched with 120 ml of saturated ammonium chloride solution. The ether layer was decanted from an offwhite solid, washed with water (400 ml), then with saturated sodium chloride solution, dried ($K_2CO_3$) and evaporated in vacuo to leave 91.9 g (85%) of an orange solid. NMR δ(CDCl$_3$) 1.57 (3H, s), 1.77 (1H, s), 1.80–2.00 (4H, m), 2.80 (2H, m), 7.08 (1H, d of d), 7.18 (1H, t of d), 7.23 (1H, t of d), 7.60 (1H, d of d).

Step 2: 1-Methyl-3,4-dihydronaphthalene

A solution of 101.9 g (0.628 mol) of 1-hydroxy-1-methyl-1,2,3,4-tetrahydronaphthalene and 1.3 g of p-toluenesulphonic acid monohydrate in 1.3 liters of toluene was heated to reflux for 3 h with water being collected by means of a Dean Stark trap. The reaction mixture was cooled, washed with water (3×400 ml), then with saturated sodium chloride solution (400 ml), dried ($K_2CO_3$) and evaporated in vacuo to leave 126.4 g of brown liquid. This was vacuum distilled to yield 78.6 g (87%) of the title product as a pale yellow oil, b.p. 59°–62° C./1 mm of Hg. NMR δ(CDCl$_3$) 2.06 (3H, m), 2.26 (2H, m), 2.76 (2H, t), 5.86 (1H, m), 7.11–7.27 (4H, m).

Step 3:
3-Butyl-1,2,3,4,5,6-hexahydro-benz[f]isoquinoline

A solution of 5.2 g (36 mmol) of 1-methyl-3,4-dihydronaphthalene and 7 g of a 37% solution of formaldehyde (86 mmol) in 60 ml of acetic acid was heated to 70° C. for 1 h with stirring. While maintaining the temperature below 70° C., 11 g (100 mmol) of n-butylamine hydrochloride was added and the mixture was stirred at 70° C. for 5 h under nitrogen. The solution was cooled to room temperature, diluted with ice-cold water (50 ml) and washed with ether (2×100 ml). The aqueous layer was made basic with 50% sodium hydroxide solution and extracted with ether (2×100 ml). The combined ether extracts were dried ($K_2CO_3$) and evaporated to dryness yielding 8.5 g of a brown oil. This was chromatographed on flash silica pre-eluted with 1% $NH_3$ (aq)/dichloromethane, eluting with 0–10% methanol/dichloromethane to give 2 g (20%) of the title product as a brown oil. The hydrochloride salt was made using ethereal hydrogen chloride. Upon evaporation of the solvent and recrystallisation from isopropanol/ether the title product hydrochloride was obtained. NMR $\delta(D_2O)$ 0.95 (3H, t), 1.25 (3H, m), 1.8 (2H, m), 2.25 (2H, t), 2.9 (5H, m), 3.3 (3H, m), 3.9 (3H, m), 7.3 (4H, m). m/z (CI+, $NH_3$) 242 (M+H)+, 198 (M—$CH_2CH_2CH_3$)+.

Step 4:
cis-3-Butyl-1,2,3,4,4a,5,6,10b-octahydrobenz[f]isoquinoline hydrochloride A mixture of 0.153 g (0.55 mmol) of 3-butyl-1,2,3,4,5,6-hexahydro-benz[f]isoquinoline hydrochloride and 0.080 g of platinum (iv) oxide in 20 ml of ethanol was hydrogenated at 50 p.s.i. overnight. The mixture was filtered and evaporated in vacuo to yield a white gum. Trituration with ether gave the title product as a white solid. NMR $\delta(D_2O)$ 0.95 (3H, t), 1.35 (3H, m), 1.6–2.2 (6H, m), 2.25–3.85 (11H, m), 7.2 (4H, m). m/z (CI+, $NH_3$) 244 (M+H)+.

EXAMPLE 2 trans-3-Butyl-1,2,3,4,4a,5,6,10b-octahydrobenz[f]isoquinoline

A solution of 0.104 g (0.374 mmol) of 3-butyl-1,2,3,4,5,6-hexahydro-benz[f]isoquinoline hydrochloride in 4 ml of anhydrous THF and 0.2 ml of aniline was added dropwise to a solution of 22 mg of lithium wire in 50 ml of liquid ammonia, cooled by a dry-ice/acetone bath. The cooling bath was then removed and the mixture was stirred under nitrogen for 2 h before quenching carefully with water (2 ml) and allowing the solvents to evaporate overnight. The residue was partitioned between ether and water, and the aqueous layer was reextracted with more ether. The combined ether extracts were dried ($K_2CO_3$) and evaporated in vacuo to leave a brown oil. This was chromatographed on flash silica eluting with 50% ethyl acetate/petroleum ether to give 31.7 mg (35%) of the title product as a colourless oil. The hydrochloride salt was made using ethereal hydrogen chloride. Upon evaporation of the solvent, the title product hydrochloride was obtained as a white solid, m.p. 217°–221° C. (dec). NMR $\delta(D_2O)$ 0.96 (3H, t, J=7 Hz), 1.41 (2H, m), 1.51–1.92 (6H, m), 2.66–2.75 (2H, m), 2.86–2.95 (3H, m), 3.12–3.19 (3H, m), 3.63 (1H, m), 3.77 (1H, m), 7.22–7.28 (3H, m), 7.34–7.37 (1H, m). m/z (CI+, $NH_3$) 244 (M+H)+, 200 (M—$CH_2CH_2CH_3$)+.

Analysis calcd. for $C_{17}H_{26}ClN$: C, 72.96; H, 9.36; N, 5.01%. Found: C, 72.86; H, 9.31; N, 4.80%.

EXAMPLE 3 trans-1,2,3,4,4a,5,6,10b-Octahydro-3-(4'-methoxybenzyl)benz[f]isoquinoline

Step 1:
1,2,3,4,5,6-Hexahydro-3-methylbenz[f]isoquinoline

Following the procedure of Example 1, step 3, 10 g (70 mmol) of 1-methyl-3,4-dihydronaphthalene and 22.55 g (278 mmol) of 37% formaldehyde solution in 60 ml of acetic acid were reacted with 10.8 g (0.16 mol) of methylamine hydrochloride. Chromatography on flash silica, eluting with 10% methanol/dichloromethane gave 6.0 g (44%) of the title product as a yellow oil. The hydrochloride salt was made using ethereal hydrogen chloride. Upon evaporation of the solvent and recrystallisation from ethyl acetate/ethanol, the title product hydrochloride was obtained, m.p. 198°–200° C. NMR $\delta(D_2O)$ 2.23 (2H, t), 2.74–3.01 (7H, m), 3.35 (1H, m), 3.72 (1H, m), 3.90–3.95 (2H, m), 7.27–7.33 (4H, m). m/z (FAB+) 200 (M+H)+.

Step 2:
trans-1,2,3,4,4a,5,6,10b-Octahydro-3-methylbenz[f]isoquinoline

Following the procedure of Example 2, 0.64 g (2.71 mmol) of 1,2,3,4,5,6-hexahydro-3-methyl-benz[f]isoquinoline hydrochloride was reacted with 0.126 g of lithium wire in 100 ml of liquid ammonia, 25 ml of anhydrous THF and 0.25 ml of aniline. Chromatography on flash silica, eluting with 5–10% methanol/dichloromethane, then on alumina, eluting with 25% ethyl acetate/petroleum ether gave 0.340 g (62%) of the title product as a colourless oil. The hydrochloride salt was made using ethereal hydrogen chloride. Upon evaporation of the solvent, the title product hydrochloride was obtained as a white solid, m.p. 277°–285° C. (dec). NMR $\delta(D_2O)$ 1.52–1.92 (4H, m), 2.63–2.75 (2H, m), 2.86–2.98 (3H, m), 2.92 (3H, s), 3.19 (1H, t of d, J=13 and 3 Hz), 3.56 (1H, m), 7.22–7.28 (3H, m), 7.33–7.36 (1H, m). m/z (CI+, $NH_3$) 202 (M+H)+.

Step 3:
trans-1,2,3,4,4a,5,6,10b-Octahydrobenz[f]isoquinoline

A solution of 0.218 g (1.08 mmol) of trans-1,2,3,4,4a,5,6,10b-octahydro-3-methyl-benz[f]isoquinoline in 3 ml of chloroform was added over 25 min to a solution of 0.140 g (1.32 mmol) of cyanogen bromide in 1 ml of chloroform under nitrogen whilst stirring magnetically. After completion of the addition, the reaction was heated to reflux for 75 min, then allowed to cool. The solvent was evaporated in vacuo, then 5 ml of 2M hydrogen chloride solution was added and the reaction was heated to reflux for 6 h, whilst stirring magnetically. After allowing to cool, the reaction mixture was made alkaline with 2M sodium hydroxide solution and extracted with ether (3×30 ml). The combined ether extracts were dried ($K_2CO_3$) and evaporated in vacuo to leave 0.186 g (92%) of the title product as a whitish solid. NMR $\delta(CDCl_3)$ 1.35–1.56 (3H, m), 1.74–1.82 (1H, m), 2.35–2.50 (3H, m), 2.78–2.92 (3H, m), 3.11 (1H, m), 3.27 (1H, m), 7.06–7.17 (3H, m), 7.24 (1H, d).

Step 4:
trans-1,2,3,4,4a,5,6,10b-Octahydro-3-(4-methoxybenzyl)-benz[f]isoquinoline To a solution of 0.175 g (0.934 mmol) of trans-1,2,3,4,4a,5,6,10b-octahydro-benz[f]isoquinoline in anhydrous DMF (10 ml) was added 0.127 ml (0.937 mmol) of 4-methoxybenzyl chloride and 0.142 g (1.03 mmol) of anhydrous potassium carbonate and the reaction was heated to 100° C. for 1 h whilst stirring magnetically under nitrogen. The solvent was then removed in vacuo and the residue was partitioned between ethyl acetate and water. The ethyl acetate layer was dried ($K_2CO_3$) and evaporated in vacuo to leave 0.243 g of an orange solid. This was chromatographed on flash silica eluting with 10–30% ethyl acetate/petroleum ether to give 0.151 g (53%) of the title product as a white solid. The hydrochloride salt was made using ethereal hydrogen chloride. Upon evaporation of the solvent the title product hydrochloride was obtained as a white solid, m.p. 267°–270.5° C. (dec). NMR $\delta(CDCl_3)$ 1.43 (1H, m), 1.80 (1H, m), 2.30–2.54 (5H, m), 2.71–3.04 (3H, m), 3.40 (1H, m), 3.64 (1H, m), 3.84 (3H, s), 4.14 (2H, m), 6.96 (2H, d, J=9 Hz), 7.09–7.14 (4H, m), 7.57 (2H, d, J=8 Hz), 12.53 (1H, m). m/z (CI+, $NH_3$) 308 $(M+H)^+$, 186 $(M-CH_2C_6H_4OCH_3)^+$, 121 $(CH_3OC_6H_4CH_2)^+$.

EXAMPLE 4
trans-3-Cyclohexyl-1,2,3,4,4a,5,6,10b-octahydrobenz[f]isoquinoline Following the procedure of Example 1, step 3, 1.00 g (6.93 mmol) of 1-methyl-3,4-dihydronaphthalene in 7 ml of acetic acid was reacted with 2.25 ml of 37% formaldehyde solution and 2.16 g of cyclohexylamine hydrochloride. Work up gave 2.41 g of crude 3-cyclohexyl-1,2,3,4,5,6-hexahydro-benz[f]isoquinoline. Following the procedure of Example 2, this was reacted with 0.397 g of lithium wire in 200 ml of liquid ammonia, 40 ml of anhydrous THF and 1 ml of aniline. Chromatography on silica, eluting with 5–10% methanol/dichloromethane, then on alumina, eluting with 5–7% ethyl acetate/petroleum ether gave 0.333 g (18%) of the title product as a white solid. The hydrochloride salt was made using ethereal hydrogen chloride. Upon evaporation of the solvent, the title product hydrochloride was obtained as a white solid, m.p. 281°–285° C. (dec). NMR $\delta(D_2O)$ 1.16–1.96 (12H, m), 2.10 (2H, m), 2.69 (2H, m), 2.92–3.05 (3H, m), 3.20–3.31 (2H, m), 3.55 (1H, m), 3.69 (1H, m), 7.25–7.29 (3H, m), 7.35–7.36 (1H, m). m/z (CI+, $NH_3$) 270 $(M+H)^+$, 226.

EXAMPLE 5
trans-3-Benzyl-1,2,3,4,4a,5,6,10b-octahydrobenz[f]isoquinoline

Following the procedure of Example 3, step 4, 40.0 mg (0.214 mmol) of trans-1,2,3,4,4a,5,6,10b-octahydrobenz[f]isoquinoline in anhydrous DMF (2 ml) was reacted with 32.5 mg (0.235 mmol) of anhydrous potassium carbonate and 25.4 ml (0.214 mmol) of benzyl bromide. Chromatography on flash silica, eluting with 10–15% ethyl acetate/petroleum ether, gave 32.0 mg (54%) of the title product as a white solid. The hydrochloride salt was made using ethereal hydrogen chloride. Upon evaporation of the solvent the title product hydrochloride was obtained as a white solid, m.p. 244°–248° C. (dec). NMR $\delta(D_2O)$ 1.49–1.84 (4H, m), 2.68 (2H, m), 2.89–2.99 (3H, m), 3.23 (1H, m), 3.53 (1H, m), 3.73 (1H, m), 4.37 (2H, m), 7.23–7.27 (3H, m), 7.33 (1H, m), 7.54 (5H, s). m/z (CI+, $NH_3$) 278 $(M+H)^+$, 186 $(M-CH_2Ph)^+$, 184, 110.

EXAMPLE 6
trans-1,2,3,4,4a,5,6,10b-Octahydro-3-phenethylbenz[f]isoquinoline

Following the procedure of Example 3, step 4, 0.307 g (1.64 mmol) of crude trans-1,2,3,4,4a,5,6,10b-octahydrobenz[f]isoquinoline in 8 ml of anhydrous DMF was reacted with 0.249 g (1.80 mmol) of anhydrous potassium carbonate and 0.222 ml (1.64 mmol) of (2-bromoethyl)benzene. Chromatography on flash silica, eluting with 20–50% ethyl acetate/petroleum ether, gave 0.12 g (25%) of the title product as a colourless oil. The hydrochloride salt was made using ethereal hydrogen chloride. Upon evaporation of the solvent the title product hydrochloride was obtained as a white solid, m.p. 277°–283° C. (dec). NMR $\delta(D_2O)$ 1.54–1.92 (4H, m), 2.72 (2H, m), 2.93–3.00 (3H, m), 3.13–3.26 (3H, m), 3.46 (2H, t), 3.71 (1H, m), 3.84 (1H, m), 7.24–7.28 (3H, m), 7.37–7.44 (6H, m). m/z (CI+, $NH_3$) 292 $(M+H)^+$, 200 $(M-CH_2Ph)^+$. Analysis calcd. for $C_{21}H_{26}ClN$: C, 76.92; H, 7.99; N, 4.27%. Found: C, 76.94; H, 7.98; N, 4.44%.

EXAMPLE 7
trans-1,2,3,4,4a,5,6,10b-Octahydro-3-(2'-picolyl)benz[f]isoquinoline Following the procedure of Example 3, step 4, 0.314 g (1.68 mmol) of crude trans-1,2,3,4,4a,5,6,10b-octahydrobenz[f]isoquinoline in 10 ml of anhydrous DMF was reacted with 0.510 g (3.69 mmol) of anhydrous potassium carbonate and 0.275 g (1.68 mmol) of 2-picolyl chloride hydrochloride. Chromatography on flash silica eluting with 5–10% methanol/dichloromethane, gave 0.064 g (14%) of the title product as a white solid. The hydrochloride salt was made using ethereal hydrogen chloride. Upon evaporation of the solvent the title product hydrochloride was obtained as a white solid, m.p. 230°–237° C. (dec). NMR $\delta(D_2O)$ 1.49–1.61 (1H, m), 1.72–1.89 (3H, m), 2.67–2.75 (2H, m), 2.89–2.93 (2H, m), 3.08 (1H, t, J=12 Hz), 3.35 (1H, t of d, J=13 Hz and 3 Hz), 3.59 (1H, m), 3.77 (1H, m), 4.59 (2H, s), 7.20–7.26 (3H, m), 7.32–7.34 (1H, m), 7.74 (1H, d of d, J=8 Hz and 5 Hz), 7.82 (1H, d, J=8 Hz), 8.20 (1H, t of d, J=8 Hz and 2 Hz), 8.74 (1H, d of d). m/z (CI+, $NH_3$) 279 $(M+H)^+$, 186 $(M-CH_2 C_5H_4N)^+$, 93. Analysis calcd. for $C_{19}H_{22}N_2$. 1:1.7 HCl: C, 67.04; H, 7.02; N, 8.23%. Found: C, 66.81; H, 7.17; N, 8.22%.

EXAMPLE 8
trans-1,2,3,4,4a,5,6,10b-Octahydro-3-(4'-nitrobenzyl)-benz[f]isoquinoline Following the procedure of Example 3, step 4, 0.153 g (0.815 mmol) of crude trans-1,2,3,4,4a, 5,6,10b-octahydrobenz[f]isoquinoline in 10 ml of anhydrous DMF was reacted with 0.124 g (0.897 mmol) of anhydrous potassium carbonate and 0.184 g (0.852 mmol) of 4-nitrobenzyl bromide. Chromatography on flash silica, eluting with 30–40% ethyl acetate/petroleum ether, gave 0.052 g (20%) of the title product as a white solid. The hydrochloride salt was made using ethereal hydrogen chloride. Upon evaporation of the solvent and recrystallisation from ethanol/ethyl acetate/methanol, the title product hydrochloride was obtained as a white solid, m.p. 198°–201° C. NMR δ(D₂O/CD₃CN) 1.45–1.57 (1H, m), 1.61–1.74 (1H, m), 1.79–1.83 (2H, m), 2.60–2.69 (2H, m), 2.88–2.94 (3H, m), 3.20 (1H, t, of d), 3.44 (1H, m), 3.64 (1H, m), 4.44 (2H, d, J=2.9 Hz), 7.17–7.22 (3H, m), 7.26–7.28 (1H, m), 7.77 (2H, d, J=8.8 Hz), 8.34 (2H, d, J=8.8 Hz). m/z (CI+, NH₃) 323 (M+H)+, 308 (M-O+H)+, 248, 211, 174, 133, 106. Analysis calcd. for C₂₂H₂₈ClN: C, 66.94; H, 6.46; N, 7.81%. Found: C, 66.83; H, 6.49; N, 7.81%.

EXAMPLE 9 trans-3-(4′-Chlorobenzyl)-1,2,3,4,4a,5,6,10b-octahydro benz[f]isoquinoline

Following the procedure of Example 3, step 4, 0.202 g (1.08 mmol) of crude trans-1,2,3,4,4a,5,6,10b-octahydro benz[f]isoquinoline in 10 ml of anhydrous DMF was reacted with 0.164 g (1.19 mmol) of anhydrous potassium carbonate and 0.183 g (1.14 mmol) of 4-chlorobenzyl chloride. Chromatography on flash silica, eluting with 30% ethyl acetate/petroleum ether, gave 0.110 g (33%) of the title product as a white solid. The hydrochloride salt was made using ethereal hydrogen chloride. Upon evaporation of the solvent the title product hydrochloride was obtained as a white solid, m.p. 257°–259° C. NMR δ(D₂O/CD₃CN) 1.51 (1H, m), 1.65 (1H, m), 1.78–1.82 (2H, m), 2.59–2.67 (2H, m), 2.80–2.89 (3H, m), 3.13 (1H, t of d), 3.41 (1H, m), 3.60 (1H, m), 4.29 (2H, d, J=3.7 Hz), 7.14–7.20 (3H, m), 7.25–7.28 (1H, m), 7.52 (4H, m). m/z (CI+, NH₃) 312 (M+H)+, 186 (M-CH₂C₆H₄Cl)+, 125. Analysis calcd. for C₂₀H₂₃Cl₂N: C, 68.97; H, 6.66; N, 4.02%. Found: C, 68.59; H, 6.63; N, 3.98%.

EXAMPLE 10 trans-3-(4′-tert-Butylbenzyl)-1,2,3,4,4a,5,6,10b-octahydro benz[f]isoquinoline

Following the procedure of Example 3, step 4, 0.300 g (1.60 mmol) of crude trans-1,2,3,4,4a,5,6,10b-octahydrobenz[f]isoquinoline in 10 ml of anhydrous DMF was reacted with 0.243 g (1.76 mmol) of anhydrous potassium carbonate and 0.310 ml (1.60 mmol) of 4-(tert-butyl)benzyl chloride. Chromatography on flash silica, eluting with 10–30% ethyl acetate/petroleum ether and 30–90% ether/petroleum ether, gave 0.142 g (27%) of the title product as a white solid. The hydrochloride salt was made using ethereal hydrogen chloride. Upon evaporation of the solvent the title product hydrochloride was obtained as a white solid, m.p. 229°–230° C. (dec). NMR δ(D₂O) 1.33 (9H, s), 1.52 (1H, m), 1.65 (1H, m), 1.72–1.84 (2H, m), 2.60–2.72 (2H, m), 2.88–2.94 (2H, m), 3.20 (1H, t of d), 3.51 (1H, m), 3.70 (1H, m), 4.33 (2H, m), 7.21–7.25 (3H, m), 7.30–7.32 (1H, m), 7.47 (2H, d, J=8.4 Hz), 7.61 (2H, d, J=8.3 Hz). m/z (CI+, NH₃) 334 (M+H)+, 233, 186 (M-CH₂C₆H₄CMe₃)+, 113.

EXAMPLE 11 trans-1,2,3,4,4a,5,6,10b-Octahydro-3-(4′-nitrophenethyl)benz[f]isoquinoline

Following the procedure of Example 3, step 4, 0.300 g (1.60 mmol) of crude trans-1,2,3,4,4a,5,6,10b-octahydrobenz[f]isoquinoline in 10 ml of anhydrous DMF was reacted with 0.244 g (1.77 mmol) of anhydrous potassium carbonate and 0.369 g (1.60 mmol) of 4-nitrophenethyl bromide. Chromatography on flash silica, eluting with 50–100% ethyl acetate/petroleum ether, then on a Lobar column, eluting with 50% ethyl acetate/petroleum ether, afforded 0.200 g (37%) of the title product as a white solid. The hydrochloride salt was made using ethereal hydrogen chloride. Upon evaporation of the solvent the title product hydrochloride was obtained as a white solid, m.p. 232°–233° C. (dec). NMR δ(CDCl₃) 1.50 (1H, m), 1.86–1.91 (1H, m), 2.28–2.61 (5H, m), 2.86–3.06 (3H, m), 3.24–3.26 (2H, m), 3.49–3.52 (2H, m), 3.66 (1H, m), 3.85 (1H, m), 7.10–7.19 (4H, m), 7.49 (2H, d, J=8.6 Hz), 8.19 (2H, d, J=8.6 Hz). m/z (CI+, NH₃) 307 (M-NO+H)+, 200 (M-CH₂C₆H₄NO₂)+, 188.

EXAMPLE 12 trans-1,2,3,4,4a,5,6,10b-Octahydro-3-phenpropylbenz[f]isoquinoline

Following the procedure of Example 3, step 4, 0.300 g (1.60 mmol) of crude trans-1,2,3,4,4a,5,6,10b-octahydrobenz[f]isoquinoline in 10 ml of anhydrous DMF was reacted with 0.244 g (1.77 mmol) of anhydrous potassium carbonate and 0.243 ml (1.60 mmol) of 1-bromo-3-phenylpropane. Chromatography on flash silica, eluting with 50–100% ethyl acetate/petroleum ether and 2–10% methanol/dichloromethane, then on a Lobar column, eluting with 50% ethyl acetate/petroleum ether, gave 0.123 g (26%) of the title product as a white solid. The hydrochloride salt was made using ethereal hydrogen chloride. Upon evaporation of the solvent and recrystallisation from ethanol/ethyl acetate, the title product hydrochloride was obtained as a white solid, m.p. 196°–201° C. NMR δ(D₂O/CD₃CN) 1.54 (1H, m), 1.68 (1H, m), 1.75–1.89 (2H, m), 2.08–2.15 (2H, m), 2.61–2.77 (4H, m), 2.84 (1H, t, J=12.2 Hz), 2.92 (2H, m), 3.08–3.18 (3H, m), 3.56 (1H, m), 3.71 (1H, m), 7.19–7.26 (3H, m), 7.29–7.33 (4H, m), 7.39–7.43 (2H, m). m/z (CI+, NH₃) 306 (M+H)+, 200 (M-CH₂CH₂Ph)+.

EXAMPLE 13 trans-3-(3′,3′-Dimethylallyl)-1,2,3,4,4a,5,6,10b-octahydrobenz[f]isoquinoline

Following the procedure of Example 3, step 4, 0.163 g (0.872 mmol) of crude trans-1,2,3,4,4a,5,6,10b-octahydrobenz[f]isoquinoline in 10 ml of anhydrous DMF was reacted with 0.133 g (0.962 mmol) of anhydrous potassium carbonate and 0.106 ml (0.917 mmol) of 4-bromo-2-methyl-2-butene. Chromatography on flash silica, eluting with 3–10% methanol/dichloromethane gave 0.036 g (16%) of the title product as a white solid. The hydrochloride salt was made using ethereal hydrogen chloride. Upon evaporation of the solvent and recrystallisation from ethanol/ethyl acetate, the title product hydrochloride was obtained as a white solid, m.p. 222°–225° C. NMR δ(D₂O/CD₃CN) 1.56 (1H, m), 1.67 (1H, m), 1.78 (3H, s), 1.86 (3H, s), 1.76–1.92 (2H, m), 2.62–2.73 (2H, m), 2.84 (1H, t, J=12.0 Hz), 2.92–2.94 (2H, m), 3.11 (1H, m), 3.53 (1H, m), 3.69 (1H, m), 3.75 (2H, d, J=7.9 Hz), 5.34 (1H, t), 7.22–7.26 (3H, m), 7.32–7.34 (1H, m). m/z (CI+, NH₃) 256 (M+H)+, 188 (M-CH₂CH=CMe₂+2H)+, 159, 130, 108, 94, 84, 70.

EXAMPLE 14 trans-3-Allyl-1, 2, 3, 4, 4a, 5, 6, 10b-octahydrobenz[f]isoquinoline

Following the procedure of Example 3, step 4, 0.152 g (0.810 mmol) of crude trans-1,2,3,4,4a,5,6,10b-octahydrobenz[f]isoquinoline in 10 ml of anhydrous DMF was reacted with 0.123 g (0.890 mmol) of anhydrous potassium carbonate and 0.074 ml (0.855 mmol) of allyl bromide. Chromatography on flash silica, eluting with 3-7% methanol/dichloromethane, then on alumina, eluting with 2-5% ethyl acetate/petroleum ether, gave 0.064 g (35%) of the title product as a colourless oil. The hydrochloride salt was made using ethereal hydrogen chloride. Upon evaporation of the solvent and recrystallisation from ethanol/ethyl acetate, the title product hydrochloride was obtained as a white solid, m.p. 204°-214° C. NMR $\delta(D_2O)$ 1.57 (1H, m), 1.69 (1H, m), 1.80-1.92 (2H, m), 2.66-2.77 (2H, m), 2.88-2.95 (3H, m), 3.18 (1H, t, J=11.4 Hz), 3.60 (1H, m), 3.77 (1H, m), 3.81 (2H, d, J=7.2 Hz), 5.60-5.65 (2H, m), 5.98 (1H, m), 7.22-7.29 (3H, m), 7.35-7.37 (1H, m). m/z (CI+, NH$_3$) 228 (M+H)$^+$. Analysis calcd. for $C_{16}H_{22}ClN$: C, 72.85; H, 8.41; N, 5.31%. Found: C, 72.84; H, 8.40; N, 5.26%.

EXAMPLE 15 trans-3-Buten-3'-yl-1,2,3,4,4a,5,6,10b-octahydrobenz[f]isoquinoline

Following the procedure of Example 3, step 4, 0.208 g (1.11 mmol) of trans-1,2,3,4,4a,5,6,10b-octahydrobenz[f]isoquinoline in 8 ml of anhydrous DMF was reacted with 0.169 g (1.22 mmol) of anhydrous potassium carbonate and 0.118 ml (1.16 mmol) of 4-bromo-1-butene. Chromatography on flash silica, eluting with 2-7% methanol/dichloromethane, then on alumina, eluting with 2-5% ethyl acetate/petroleum ether, afforded 0.167 g (62%) of the title product as a colourless oil. The hydrochloride salt was made using ethereal hydrogen chloride. Upon evaporation of the solvent the title product hydrochloride was obtained as a white solid, m.p. 195°-209° C. NMR $\delta(D_2O)$ 1.57 (1H, m), 1.70 (1H, m), 1.81-1.92 (2H, m), 2.59 (2H, q, J=7.3 Hz), 2.66-2.76 (2H, m), 2.89-2.95 (3H, m), 3.19 (1H, t, J=12.6 Hz), 3.28 (2H, t, J=7.6 Hz), 3.65 (1H, m), 3.80 (1H, m), 5.21-5.31 (2H, m), 5.85 (1H, m), 7.22-7.30 (3H, m), 7.35-7.37 (1H, m). m/z (CI+, NH$_3$) 242 (M+H)$^+$, 200 (M-CH$_2$CH=CH$_2$)$^+$. Analysis calcd. for $C_{17}H_{24}ClN$: C, 73.49; H, 8.71; N, 5.04%. Found: C, 73.34; H, 8.62; N, 4.96%.

EXAMPLE 16 trans-1,2,3,4,4a,5,6,10b-Octahydro-3-(2'-thiophenemethyl)-benz[f]isoquinoline

To a solution of 0.179 g (0.954 mmol) of trans-1,2,3,4,4a,5,6,10b-octahydrobenz[f]isoquinoline in anhydrous dichloromethane (8 ml), under nitrogen, was added 0.332 ml (2.38 mmol) of triethylamine, then 0.204 ml (1.91 mmol) of 2-thiophenecarbonyl chloride and the reaction was stirred for 2½ h. The solvent was evaporated in vacuo and the residue was partitioned between ether and water. The ether layer was dried (MgSO$_4$) and evaporated in vacuo to leave 0.392 g of an oil.

This was dissolved in anhydrous THF (15 ml) and 2.9 ml of a 1.0M solution of lithium aluminium hydride in THF was added dropwise, under nitrogen. The reaction was stirred for 2 h, then heated to reflux for 1 h, before quenching with ethyl acetate (2 ml). The inorganic salts were precipitated with saturated ammonium chloride solution (1 ml) and the mixture was filtered, washing the solid with ethyl acetate. The filtrate was evaporated in vacuo to leave 0.338 g of a pale yellow oil. Chromatography on flash silica, eluting with 30% ethyl acetate/petroleum ether, gave 0.046 g (17%) of the title product as a white solid. The hydrochloride salt was made using ethereal hydrogen chloride. Upon evaporation of the solvent the title product hydrochloride was obtained as a white solid, m.p. 196°-213° C. NMR $\delta(D_2O/CD_3CN)$ 1.54 (1H, m), 1.68 (1H, m), 1.79-1.87 (2H, m), 2.61-2.73 (2H, m), 2.89-2.95 (3H, m), 3.20 (1H, t), 3.54 (1H, m), 3.72 (1H, m), 4.61 (2H, s), 7.18-7.25 (4H, m), 7.30-7.33 (1H, m), 7.36 (1H, d, J=2.9 Hz), 7.65 (1H, d of d, J=5.2 and 1.1 Hz). m/z (CI+, NH$_3$) 284 (M+H)$^+$, 182, 164, 138, 106. Analysis calcd. for $C_{18}H_{22}ClNS$: C, 67.58; H, 6.93; N, 4.38%. Found: C, 67.80; H, 6.92; N, 4.58%.

EXAMPLE 17 trans-3-Furfuryl-1,2,3,4,4a,5,6,10b-octahydrobenz[f]isoquinoline

Following the procedure of Example 16, 0.168 g (0.897 mmol) of trans-1,2,3,4,4a,5,6,10b-octahydrobenz[f]isoquinoline in 8 ml of anhydrous dichloromethane was reacted with 0.313 ml (2.25 mmol) of triethylamine and 0.177 ml (1.80 mmol) of 2-furoyl chloride for 1½ h, then with 2.7 ml of a 1.0M solution of lithium aluminium hydride in THF for 30 minutes at room temperature and 1 h at reflux. Chromatography on flash silica, eluting with 30-40% ethyl acetate/petroleum ether, afforded 0.091 g (38%) of the title product as a white solid. The hydrochloride salt was made using ethereal hydrogen chloride. Upon evaporation of the solvent the title product hydrochloride was obtained as a white solid, m.p. 214°-223° C. (dec). NMR $\delta(D_2O)$ 1.55 (1H, m), 1.68 (1H, m), 1.79-1.90 (2H, m), 2.62-2.75 (2H, m), 2.91-2.99 (3H, m), 3.23 (1H, t, J=11.8 Hz), 3.54 (1H, m), 3.72 (1H, m), 4.44 (2H, s), 6.57 (1H, d of d, J=3.3 and 1.9 Hz), 6.75 (1H, d, J=3.2 Hz), 7.21-7.28 (3H, m), 7.33-7.36 (1H, m), 7.67 (1H, d, J=1.8 Hz). m/z (CI+, NH$_3$) 268 (M+H)$^+$, 200 (M-C$_4$H$_3$O)$^+$, 124, 96, 81.

EXAMPLE 18 trans, 1,2,3,4,4a,5,6,10b-Octahydro-3-propyl-benz[f]isoquinoline

Following the procedure of Example 1, step 3, 1.04 g (7.19 mmol) of 1-methyl-3,4-dihydronaphthalene in 7 ml of acetic acid was reacted with 2.33 ml of 37% formaldehyde solution and 1.58 g of propylamine hydrochloride. Work up gave 1.98 g of crude 1,2,3,4,5,6-hexahydro-3-propyl-benz[f]isoquinoline. Following the procedure of Example 2, this was reacted with 0.435 g of lithium wire in 250 ml of liquid ammonia, 40 ml of anhydrous THF and 1 ml of aniline. Chromatography on flash silica, eluting with 5-10% methanol/dichloromethane, then on alumina, eluting with 2-5% ethyl acetate/petroleum ether, gave 0.497 g (30%) of the title product as a colourless oil. The hydrochloride salt was made using ethereal hydrogen chloride. Upon evaporation of the solvent, the title product hydrochloride was obtained as a white solid, m.p. 257°-259° C. (dec). NMR $\delta(D_2O)$ 1.00 (3H, t, J=7.4 Hz), 1.57 (1H, m), 1.68-1.92 (5H, m), 2.66-2.76 (2H, m), 2.87-2.95 (3H, m), 3.12-3.16 (3H, m), 3.63 (1H, m), 3.77 (1H, m), 7.22-7.31 (3H, m), 7.35-7.38 (1H, m). m/z (CI+, NH$_3$) 230 (M+H)$^+$, 200 (M-CH$_2$CH$_3$)$^+$. Analysis calcd. for $C_{16}H_{24}ClN$: C, 72.29; H, 9.10; N, 5.27%. Found: C, 72.07; H, 9.01; N, 5.19%.

EXAMPLE 19 trans-3-(1'-Adamantyl)-1,2,3,4,4a,5,6,10b-octahydrobenz[f]isoquinoline

Following the procedure of Example 1, step 3, 2.05 g (14.0 mmol) of 1-methyl-3,4-dihydronaphthalene in 14 ml of acetic acid was reacted with 4.54 ml of 37% formaldehyde solution and 6.03 g of 1-adamantanamine hydrochloride. Work up gave 5.58 g of crude 3-(1-adamantyl)-1,2,3,4,5,6-hexahydrobenz[f]isoquinoline. Following the procedure of Example 2, this was reacted with 1.02 g of lithium wire in 400 ml of liquid ammonia, 100 ml of anhydrous THF and 2 ml of aniline. Chromatography on flash silica, eluting with 5–20% methanol/dichloromethane, then on alumina, eluting with 2–7% ethyl acetate/petroleum ether, afforded 0.54 g (12%) of the title product as a white solid. The hydrochloride salt was made using ethereal hydrogen chloride. Upon evaporation of the solvent and recrystallisation from methanol/petroleum ether, the title product hydrochloride was obtained as a white solid, m.p. 252°–255° C. NMR $\delta(D_2O, CD_3CN)$ 1.56 (1H, m), 1.68–1.92 (9H, m), 2.02–2.04 (6H, m), 2.27 (3H, s), 2.61 (1H, m), 2.74 (1H, d of d), 2.82 (1H, t, J=12.0 Hz), 2.92–2.95 (2H, m), 3.08 (1H, t of d), 3.65 (1H, m), 3.82 (1H, m), 7.19–7.23 (3H, m), 7.29–7.30 (1H, m). m/z (CI+, NH$_3$) 322 (M+H)$^+$, 195. Analysis calcd. for $C_{23}H_{32}ClN$: C, 77.17; H, 9.01; N, 3.91%. Found: C, 77.09; H, 8.95; N, 3.89%.

EXAMPLE 20 trans-3-(2'-Adamantyl)-1,2,3,4,4a,5,6,10b-octahydrobenz[f]isoquinoline

Following the procedure of Example 1, step 3, 5.00 g (34.7 mmol) of 1-methyl-3,4-dihydronaphthalene in 35 ml of acetic acid was reacted with 11.3 ml of 37% formaldehyde solution and 14.96 g of 2-adamantanamine hydrochloride. Work up gave 14.47 g of crude 3-(2-adamantyl)-1,2,3,4,4a,5,6,10b-octahydrobenz[f]isoquinoline. Following the procedure of Example 2, this was reacted with 2.09 g of lithium wire in 500 ml of liquid ammonia, 200 ml of anhydrous THF and 5 ml of aniline. Chromatography on flash silica, eluting with 2–10% methanol/dichloromethane, then on alumina, eluting with 0–4% ethyl acetate/petroleum ether, gave 2.73 g (24%) of the title product as a white solid. The hydrochloride salt was made using ethereal hydrogen chloride. Upon evaporation of the solvent and recrystallisation from ethanol/ethyl acetate/petroleum ether, the title product hydrochloride was obtained as a white solid, m.p. 247°–252° C. NMR $\delta(D_2O/CD_3CN)$ 1.52 (1H, m), 1.69–1.98 (15H, m), 2.48 (2H, s), 2.59–2.75 (3H, m), 2.91–3.09 (3H, m), 3.29–3.34 (1H, m), 3.79 (1H, m), 3.95 (1H, m), 7.18–7.24 (3H, m), 7.30–7.33 (1H, m). m/z (CI+, NH$_3$) 322 (M+H)$^+$.

EXAMPLE 21 trans-3-Butyl-1,2,3,4,4a,5,6,10b-octahydro-7,9-dimethyl benz[f]isoquinoline

Step 1:
1-Hydroxy-1,5,7-trimethyl-1,2,3,4-tetrahydronaphthalene

Following the procedure of Example 1, step 1, 25.20 g (0.145 ml) of 5,7-dimethyltetralone in 200 ml of anhydrous ether was reacted with 60.3 ml of 3.0M methyl magnesium bromide in ether to give 26.64 g (97%) of the title product as an orange oil. NMR $\delta(CDCl_3)$ 1.56 (3H, s), 1.70 (1H, s), 1.78–2.04 (4H, m), 2.20 (3H, s), 2.30 (3H, s), 2.60 (2H, m), 6.90 (1H, s), 7.30 (1H, s).

Step 2: 1,5,7-Trimethyl-3,4-dihydronaphthalene

Following the procedure of Example 1, step 2, 26.64 g (0.140 mol) of 1-hydroxy-1,5,7-trimethyl-1,2,3,4-tetrahydronaphthalene in 300 ml of toluene was reacted with 0.30 g of p-toluenesulphonic acid monohydrate. Vacuum distillation yielded 20.49 g (85%) of the title product as a pale yellow liquid, b.p. 67°–70° C./0.12 mm of Hg. NMR $\delta(CDCl_3)$ 2.04 (3H, m), 2.21–2.25 (2H, m), 2.25 (3H, s), 2.30 (3H, s), 2.66 (2H, t, J=8.1 Hz), 5.83 (1H, m), 6.87 (1H, s), 6.94 (1H, s).

Step 3: trans-3-Butyl-1,2,3,4,4a,5,6,10b-octahydro-7,9-dimethyl-benz[f]isoquinoline Following the procedure of Example 1, step 3, 1.064 g (6.18 mmol) of 1,5,7-trimethyl-3,4-dihydronaphthalene in 7 ml of acetic acid was reacted with 2.0 ml of 37% formaldehyde solution and 1.557 g of butylamine hydrochloride. Work up gave 1.89 g of crude 3-butyl-1,2,3,4,5,6-hexahydro-7,9-dimethyl-benz[f]isoquinoline. Following the procedure of Example 2, this was reacted with 0.511 g of lithium wire in 200 ml of liquid ammonia, 40 ml of anhydrous THF and 1 ml of aniline. Chromatography on flash silica, eluting with 5–10% methanol/dichloromethane, then on alumina, eluting with 2–3% ethyl acetate/petroleum ether, afforded 0.253 g (15%) of the title product as a colourless oil. The hydrochloride salt was made using ethereal hydrogen chloride. Upon evaporation of the solvent, the title product hydrochloride was obtained as a white solid, m.p. 260°–263° C. (dec). NMR $\delta(D_2O)$ 0.94 (3H, t, J=7.4 Hz), 1.40 (2H, m), 1.50 (1H, m), 1.61 (1H, m), 1.70–1.78 (3H, m), 1.91–1.96 (1H, m), 2.18 (3H, s), 2.28 (3H, s), 2.56–2.72 (3H, m), 2.77–2.86 (2H, m), 3.08–3.17 (3H, m), 3.61 (1H, m), 3.74 (1H, m), 7.01 (1H, s), 7.06 (1H, s). m/z (CI+NH$_3$) 272 (M+H)$^+$, 228 (M-CH$_2$CH$_2$CH$_3$)$^+$, 149, 108.

EXAMPLE 22 trans-1,2,3,4,4a,5,6,10b-Octahydro-3-(2'-naphthylmethyl)benz[f]isoquinoline

Following the procedure of Example 3, step 4, 0.370 g (1.98 mmol) of trans-1,2,3,4,4a,5,6,10b-octahydrobenz[f]isoquinoline in 20 ml of anhydrous DMF was reacted with 0.311 g (2.39 mmol) of anhydrous potassium carbonate and 0.486 g (2.20 mmol) of 2-(bromomethyl)naphthalene at 100° C. for 2 h. Chromatography on flash silica, eluting with 10–20% ethyl acetate/petroleum ether gave the title product as an oil. The hydrochloride salt was made using ethereal hydrogen chloride. Upon evaporation of the solvent, washing with ether and recrystallisation from ethanol/ethyl acetate/petroleum ether, 0.110 g (15%) of the title product hydrochloride was obtained as a white solid, m.p. 175°–177° C. NMR $\delta(D_2O)$ 1.56 (1H, m), 1.67 (1H, m), 1.73–1.84 (2H, m), 2.64–2.74 (2H, m), 2.89 (2H, m), 3.00 (1H, t), 3.28 (1H, m), 3.57 (1H, m), 3.77 (1H, m), 4.54 (2H, m), 7.20–7.26 (3H, m), 7.31–7.34 (1H, m), 7.60–7.67 (3H, m), 8.01–8.09 (4H, m). m/z (CI+, NH$_3$) 328 (M+H)$^+$, 194,141. Analysis calcd. for $C_{24}H_{26}NCl$: C, 79.21; H, 7.20; N, 3.85%. Found: C, 78.97; H, 7.27; N, 3.76%.

EXAMPLE 23 trans-3-Cyclopropylmethyl-1,2,3,4,4a,5,6,10b-octahydrobenz[f]isoquinoline

To a solution of 0.200 g (1.07 mmol) of trans-1,2,3,4,4a,5,6,10b-octahydrobenz[f]isoquinoline in anhydrous dichloromethane (20 ml) was added 0.200 g (1.48 mmol) of (bromomethyl)cyclopropane and the reaction mixture was left to stand for 24 h. The solvent was removed in vacuo and the residue was chromatographed on flash silica, eluting with 10% methanol/dichloromethane to give 0.160 g (62%) of the title product as an oil. The hydrochloride salt was made using ethereal hydrogen chloride. Upon evaporation of the solvent, washing with ether and recrystallisation from ethanol/ethyl acetate/petroleum ether, the title product hydrochloride was obtained as a white sold, m.p. 255°–257° C. NMR δ(D$_2$O) 0.43 (2H, m), 0.78 (2H, m), 1.17 (1H, m), 1.58 (1H, m), 1.80–1.94 (2H, m), 2.67–2.77 (2H, m), 2.90–2.97 (3H, m), 3.09 (2H, d, J=7.4 Hz), 3.20 (1H, t of d, J=13.1 and 3.0 Hz), 3.74 (1H, m), 3.87 (1H, m), 7.22–7.31 (3H, m), 7.36–7.38 (1H, m). m/z (CI+, NH$_3$) 242 (M+H)+, 182, 165.

EXAMPLE 24

Tablet Preparation

Tablets containing 1.0, 2.0, 25.0, 26.0, 50.0 and 100.0 mg, respectively, of trans-3-Butyl-1,2,3,4,4a,5,6,10b-octahydro-benz[f]isoquinoline and trans-3-Cyclohexyl-1,2,3,4,4a,5,6,10b-octahydro-benz[f]isoquinoline are prepared as illustrated below.

| | Amount-mg. | | |
|---|---|---|---|
| TABLE FOR DOSES CONTAINING FROM 1-25 MG OF THE ACTIVE COMPOUND | | | |
| Active Compound | 1.0 | 2.0 | 25.0 |
| Microcrystalline cellulose | 49.25 | 48.75 | 37.25 |
| Modified food corn starch | 49.25 | 48.75 | 37.25 |
| Magnesium stearate | 0.50 | 0.50 | 0.50 |
| TABLE FOR DOSES CONTAINING FROM 26-100 MG OF THE ACTIVE COMPOUND | | | |
| Active Compound | 26.0 | 50.0 | 100.0 |
| Microcrystalline cellulose | 52.0 | 100.0 | 200.0 |
| Modified food corn starch | 2.21 | 4.25 | 8.5 |
| Magnesium stearate | 0.39 | 0.75 | 1.5 |

All of the active compound, lactose, and a portion of the corn starch are mixed and granulated to 10% corn starch paste. The resulting granulation is sieved, dried and blended with the remainder of the corn starch and the magnesium stearate. The resulting granulation is then compressed into tablets.

What is claimed is:

1. A compound of formula II:

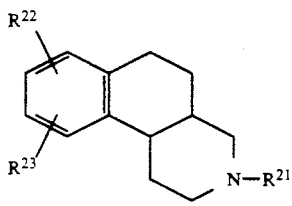

(II)

wherein R$^{21}$ is selected from the group consisting of C$_{3-6}$ alkyl, C$_{2-6}$ alkenyl, C$_{3-7}$ cycloalkyl, C$_{3-7}$ cycloalkyl(C$_{1-6}$)alkyl, or aryl(C$_{1-6}$)alkyl, any of which groups may be optionally substituted with a substituent selected from the group consisting of C$_{1-6}$ alkyl, adamantyl, phenyl, halogen, C$_{1-6}$ haloalkyl, trifluoromethyl, hydroxy, C$_{1-6}$ alkoxy, aryloxy, C$_{1-3}$ alkylenedioxy, nitro, cyano, carboxy, C$_{2-6}$ alkoxycarbonyl, C$_{2-6}$ alkoxycarbonyl(C$_{1-6}$)alkyl, C$_{2-6}$ alkylcarbonyloxy, C$_{1-6}$ alkylthio, C$_{1-6}$ alkylsulphinyl, C$_{1-6}$ alkylsulphonyl, amino, mono- or di(C$_{1-6}$)alkylamino, C$_{2-6}$ alkylcarbonylamino and C$_{2-6}$ alkoxycarbonylamino; and R$^{22}$ and R$^{23}$ are hydrogen; or a pharmaceutically acceptable salt thereof.

2. The compound according to claim 1, wherein the ring junction at positions 4a and 10b is trans.

3. The compound represented by formula IIA:

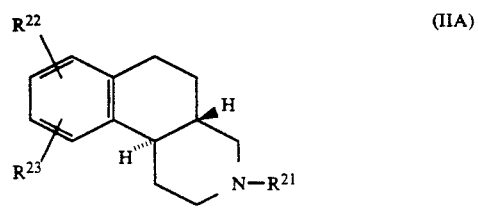

(IIA)

wherein, R$^{21}$ is selected from the group consisting of C$_{3-6}$ alkyl, C$_{2-6}$ alkenyl, C$_{3-7}$ cycloalkyl, C$_{3-7}$ cycloalkyl-(C$_{1-6}$) alkyl and aryl (C$_{1-6}$) alkyl, any of said groups may be optionally substituted with a substituent selected from the group consisting of C$_{1-6}$ alkyl, adamantyl, phenyl, halogen, C$_{1-6}$ haloalkyl, trifluoromethyl, hydroxy, C$_{1-6}$ alkoxy, aryloxy, C$_{1-3}$ alkylenedioxy, nitro, cyano, carboxy, C$_{2-6}$ alkoxycarbonyl, C$_{2-6}$ alkoxycarbonyl (C$_{1-6}$) alkyl, C$_{2-6}$ alkylcarbonyloxy, arylcarbonyloxy, C$_{1-6}$ alkylthio, C$_{1-6}$ alkylsulphinyl, C$_{1-6}$ alkylsulphonyl, C$_{2-6}$ alkylcarbonyl, amino, mono- or di(C$_{1-6}$) alkylamino, C$_{2-6}$ alkylcarbonylamino and C$_{2-6}$ alkoxycarbonylamino and R$^{22}$ and R$^{23}$ are hydrogen; or pharmaceutically acceptable salts thereof.

4. The compound according to claim 3, wherein R$^{21}$ is selected from the group consisting of n-propyl, n-butyl, allyl, dimethylallyl, butenyl, cyclohexyl, adamantyl, cyclopropylmethyl, benzyl, methylbenzyl, t-butylbenzyl, chlorobenzyl, nitrobenzyl, methoxybenzyl, phenethyl, (nitrophenyl) ethyl, phenylpropyl, and naphthylmethyl.

5. The compound according to claim 1 represented by formula IIB;

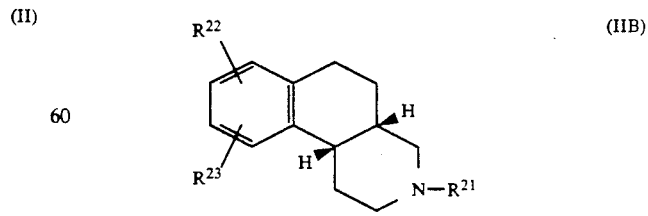

(IIB)

wherein, R$^{21}$ is defined as in claim 1, R$^{22}$ and R$^{23}$ are both hydrogen.

6. A compound of formula II:

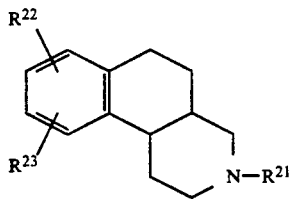

selected from the group consisting of
3-butyl-1,2,3,4,4a,5,6,10b-octahydrobenz isoquinoline;
3-(4'-methoxybenzyl)-1,2,3,4,4a,5,6,10b-octahydrobenz isoquinoline;
3-cyclohexyl-1,2,3,4,4a,5,6,10b-octahydrobenz isoquinoline;
3-benzyl-1,2,3,4,4a,5,6,10b-octahydrobenz isoquinoline;
1,2,3,4,4a,5,6,10b-octahydro-3-phenethylbenz isoquinoline;
3-(4'-nitrobenzyl)-1,2,3,4,4a,5,6,10b-octahydrobenz isoquinoline;
3-(4'-chlorobenzyl)-1,2,3,4,4a,5,6,10b-octahydrobenz isoquinoline;
3-(4'-t-butylbenzyl)-1,2,3,4,4a,5,6,10b-octahydrobenz isoquinoline;
3-1,2,3,4,4a,5,6,10b-octahydrobenz isoquinoline;
1,2,3,4,4a,5,6,10b-octahydro-3-(3'-phenylpropyl)-benz isoquinoline;
3-(3'-methylbut-2'-enyl)-1,2,3,4,4a,5,6,10b-octahydrobenz isoquinoline;
1,2,3,4,4a,5,6,10b-octahydro-3-(prop-2'-enyl)-benz isoquinoline;
3-(but-3'-enyl)-1,2,3,4,4a,5,6,10b-octahydrobenz isoquinoline;
1,2,3,4,4a,5,6,10b-octahydro-3-propylbenz isoquinoline;
3-(1'-adamantyl)-1,2,3,4,4a,5,6,10b-octahydrobenz isoquinoline;
3-(2'-adamantyl)-1,2,3,4,4a,5,6,10b-octahydrobenz isoquinoline;
3-butyl-7,9-dimethyl-1,2,3,4,4a,5,6,10b-octahydrobenz isoquinoline;
3-(2'-naphthylmethyl)-1,2,3,4,4a,5,6,10b-octahydrobenz isoquinoline;
3-cyclopropylmethyl-1,2,3,4,4a,5,6,10b-octahydrobenz isoquinoline;
and salts thereof.

7. A pharmaceutical composition comprising an effective amount of a compound represented by formula IA:

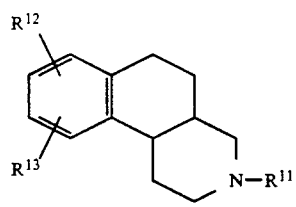

wherein, $R^{11}$ is selected from the group consisting of $C_{3-6}$ alkyl, $C_{2-6}$ alkenyl, $C_{3-7}$ cycloalkyl, $C_{3-7}$ cycloalkyl($C_{1-6}$)alkyl, or aryl($C_{1-6}$)alkyl, any of which groups may be optionally substituted with a substituent selected from the group consisting of $C_{1-6}$ alkyl, adamantyl, phenyl, halogen, $C_{1-6}$ haloalkyl, trifluoromethyl, hydroxy, $C_{1-6}$ alkoxy, aryloxy, $C_{1-3}$ alkylenedioxy, nitro, cyano, carboxy, $C_{2-6}$ alkoxycarbonyl, $C_{2-6}$ alkoxycarbonyl($C_{1-6}$)alkyl, $C_{2-6}$ alkylcarbonyloxy, $C_{1-6}$ alkylthio, $C_{1-6}$ alkylsulphinyl, $C_{1-6}$ alkylsulphonyl, amino, mono- or di($C_{1-6}$)alkylamino, $C_{2-6}$ alkylcarbonylamino and $C_{2-6}$ alkoxycarbonylamino; and $R^{12}$ and $R^{13}$ are hydrogen; or a pharmaceutically acceptable salt thereof.

8. A method for the treatment of disorders requiring administration of a selective ligand at sigma recognition sites which comprises administering to a patient in need of such treatment an effective amount of a compound of formula I:

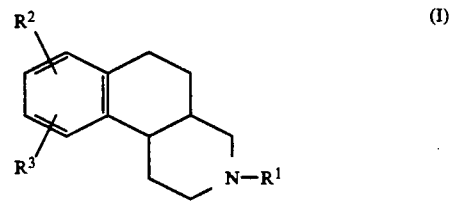

wherein $R^1$ is a hydrocarbon selected from the group consisting of $C_{1-6}$ alkyl, $C_{2-6}$ alkenyl, $C_{2-6}$ alkynyl, $C_{3-10}$ cycloalkyl, $C_{3-7}$ cycloalkyl($C_{1-6}$)alkyl, aryl, or aryl($C_{1-6}$) alkyl, any of which groups may be optionally substituted by one or more groups selected from the group consisting of $C_{1-6}$ alkyl, adamantyl, phenyl, halogen, $C_{1-6}$ haloalkyl, trifluoromethyl, hydroxy, $C_{1-6}$ alkoxy, aryloxy, keto, $C_{1-3}$ alkylenedioxy, nitro, cyano, carboxy, $C_{2-6}$ alkoxycarbonyl, $C_{2-6}$ alkoxycarbonyl($C_{1-6}$)alkyl, $C_{2-6}$ alkylcarbonyloxy, arylcarbonyloxy, $C_{2-6}$ alkylcarbonyl, arylcarbonyl, $C_{1-6}$ alkylthio, $C_{1-6}$ alkylsulphinyl, $C_{1-6}$ alkylsulphonyl, amino, mono-or di($C_{1-6}$)alkylamino, $C_{2-6}$ alkylcarbonylamino and $C_{2-6}$ alkoxycarbonylamino; $R^2$ and $R^3$ are independently selected from the group consisting of hydrogen, hydrocarbons consisting of $C_{1-6}$ alkyl, $C_{2-6}$ alkenyl, $C_{2-6}$ alkynyl, $C_{3-10}$ cycloalkyl, $C_{3-7}$ cycloalkyl($C_{1-6}$)alkyl, aryl, or aryl($C_{1-6}$)alkyl, halogen, cyano, trifluoromethyl, nitro, —$OR^x$, $SR^x$, —$NR^xR^y$, —$CO_2R^x$, —$CONR^xR^y$ or together represent methylenedioxy; and Rx and Ry independently represent hydrogen or hydrocarbons selected from the group consisting of $C_{1-6}$ alkyl, $C_{2-6}$ alkenyl, $C_{2-6}$ alkynyl, $C_{3-10}$ cycloalkyl, $C_{3-7}$ cycloalkyl($C_{1-6}$)alkyl, aryl, or aryl($C_{1-6}$)alkyl, or a pharmaceutically acceptable salt thereof.

9. A method according to claim 8 wherein the ring junction at positions 4a and 10b of the compound is trans.

10. A method according to claim 8 wherein the compound is represented by formula IIIA and salts thereof:

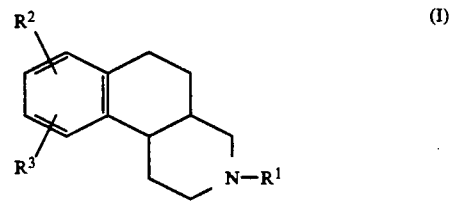

(Note: formula IIIA)

wherein $R^1$ is selected from the group consisting of $C_{3-6}$ alkyl, $C_{2-6}$ alkenyl, $C_{3-7}$ cycloalkyl, $C_{3-7}$ cycloalkyl($C_{1-6}$)alkyl and aryl($C_{1-6}$)alkyl and any of which groups may be optionally substituted; and $R^2$ and $R^3$ are as defined in claim 8.

11. A method according to claim 10 wherein $R^1$ of the compound is selected from the group consisting of n- propyl, n-butyl, allyl, dimethylallyl, butenyl, cyclohexyl, adamantyl, cyclopropylmethyl, benzyl, methylbenzyl, t-butylbenzyl, chlorobenzyl, nitrobenzyl, methoxybenzyl, phenethyl, (nitrophenyl)ethyl, phenylpropyl and naphthylmethyl.

12. A method according to claim 8 wherein the compound is represented by formula IIIB and salts thereof:

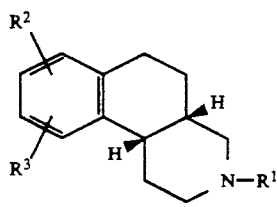

(IIIB)

wherein $R^1$, $R^2$ and $R^3$ are defined in claim 8.

13. A method according to claim 8 wherein the compound is selected from the group consisting of:
3-butyl-1,2,3,4,4a,5,6,10b-octahydrobenz [f]isoquinoline;
3-(4'-methoxybenzyl)-1,2,3,4,4a,5,6,10b-octahydrobenz[f]isoquinoline;
3-cyclohexyl-1,2,3,4,4a,5,6,10b-octahydrobenz[f]isoquinoline;
3-benzyl-1,2,3,4,4a,5,6,10b-octahydrobenz[f] isoquinoline;
1,2,3,4,4a,5,6,10b-octahydro-3-phenethylbenz[f]isoquinoline;
1,2,3,4,4a,5,6,10b-octahydro-3-(2'-picolyl)benz[f]isoquinoline;
3-(4'-nitrobenzyl)-1,2,3,4,4a,5,6,10b-octahydrobenz[f]isoquinoline;
3-(4'-chlorobenzyl)-1,2,3,4,4a,5,6,10b-octahydrobenz[f]isoquinoline;
3-(4'-t-butylbenzyl)-1,2,3,4,4a,5,6,10b-octahydrobenz[f]isoquinoline;
3-[2'-(4-nitrophenyl)ethyl]1,2,3,4,4a,5,6,10b-octahydrobenz[f] isoquinoline;
1,2,3,4,4a,5,6,10b-octahydro-3-(3'-phenylpropyl)benz[f]isoquinoline;
3-(3'-methylbut-2'-enyl)-1,2,3,4,4a,5,6,10b-octahydrobenz[f]isoquinoline;
1,2,3,4,4a,5,6,10b-octahydro-3-(prop-2'-enyl)benz[f]isoquinoline;
3-(but-3'-enyl)-1,2,3,4,4a,5,6,10b-octahydrobenz[f]isoquinoline;
1,2,3,4,4a,5,6,10b-octahydro-3-propylbenz[f]isoquinoline;
3-(1'-adamantyl)-1,2,3,4,4a,5,6,10b-octahydrobenz[f]isoquinoline;
3-(2'-adamantyl)-1,2,3,4,4a,5,6,10b-octahydrobenz[f]isoquinoline;
3-butyl-7,9-dimethyl-1,2,3,4,4a,5,6,10b-octahydrobenz[f]isoquinoline;
3-(2'-naphthylmethyl)-1,2,3,4,4a,5,6,10b-octahydrobenz[f]isoquinoline;
3-cyclopropylmethyl-1,2,3,4,4a,5,6,10b-octahydrobenz[f]isoquinoline;
and salts thereof.

* * * * *